(12) United States Patent
Meyers et al.

(10) Patent No.: US 11,602,565 B2
(45) Date of Patent: Mar. 14, 2023

(54) BAMBOO EXTRACT ANTI-CAKING AND FLOW AGENTS FOR DRY POWDERED FOODS, FOOD INGREDIENTS, PHARMACEUTICALS AND NUTRACEUTICALS

(71) Applicant: Griffith Foods International Inc., Alsip, IL (US)

(72) Inventors: Gregory J. Meyers, Alsip, IL (US); Samantha L. Amos, Alsip, IL (US)

(73) Assignee: Griffith Foods International, Inc., Alsip, IL (US)

( * ) Notice: Subject to any disclaimer, the term of this patent is extended or adjusted under 35 U.S.C. 154(b) by 0 days.

(21) Appl. No.: 16/782,564

(22) Filed: Feb. 5, 2020

(65) Prior Publication Data
US 2020/0246469 A1 Aug. 6, 2020

Related U.S. Application Data

(60) Provisional application No. 62/949,602, filed on Dec. 18, 2019, provisional application No. 62/836,487, filed on Apr. 19, 2019, provisional application No. 62/801,352, filed on Feb. 5, 2019.

(51) Int. Cl.
| | |
|---|---|
| *A61K 47/46* | (2006.01) |
| *A23L 29/00* | (2016.01) |
| *A61K 45/06* | (2006.01) |
| *A61K 47/02* | (2006.01) |
| *A61K 47/26* | (2006.01) |

(52) U.S. Cl.
CPC ............ *A61K 47/46* (2013.01); *A23L 29/035* (2016.08); *A61K 45/06* (2013.01); *A61K 47/02* (2013.01); *A61K 47/26* (2013.01); *A23V 2002/00* (2013.01)

(58) Field of Classification Search
CPC ........ A61K 47/04; A61K 47/02; A61K 47/46; A23L 33/105; A23L 27/77; A23P 10/43
See application file for complete search history.

(56) References Cited

U.S. PATENT DOCUMENTS

| | | | |
|---|---|---|---|
| 6,436,461 B1 | 8/2002 | Bouwmeesters et al. | |
| 7,829,053 B2 | 11/2010 | Constantz et al. | |
| 2010/0239487 A1 | 9/2010 | Constantz et al. | |
| 2014/0212453 A1 | 7/2014 | Chang | |
| 2015/0201661 A1* | 7/2015 | Heuer .................. | A23K 20/10 424/750 |
| 2016/0040001 A1 | 2/2016 | Desille et al. | |
| 2017/0027168 A1 | 2/2017 | Heath | |
| 2017/0081500 A1 | 3/2017 | Bredt et al. | |
| 2017/0258706 A1 | 9/2017 | Hili et al. | |

FOREIGN PATENT DOCUMENTS

| | | |
|---|---|---|
| CN | 204769023 U | 11/2015 |
| CN | 103549365 B | 5/2016 |
| CN | 107496725 A | 12/2017 |
| CN | 207828150 U | 9/2018 |
| DE | 20302508 U1 | 5/2003 |
| JP | 2006028452 | 2/2006 |
| JP | 3793783 B2 | 7/2006 |
| JP | 2010036529 A2 | 2/2010 |
| KR | 20160060459 A | 5/2016 |
| WO | WO 02/090025 A1 | 11/2002 |
| WO | WO 2008/016701 A2 | 2/2008 |

OTHER PUBLICATIONS

TIC Gums Nutriloid® Bamboo Fiber, (https://plus.google.com/105963033572941111018), 1p. downloaded Jun. 10, 2019.
Josef Ehrler GmbH & Xo. KG, Anti-Caking Agent for Foods and Spices: Natural Cellulose Powder, May 17, 2019.
Steinhauer et al., Sanacel® Fibres in Powder Mixtures and Spices Anticaking & Antidusting, 6 pgs., 2016.
International Search Report and Written Opinion of PCT application PCT/US2020/016726 dated Jun. 3, 2020, 11 pages.

* cited by examiner

*Primary Examiner* — Carlos A Azpuru
(74) *Attorney, Agent, or Firm* — Crowell & Moring LLP

(57) ABSTRACT

An anti-caking or flow agent is provided herein. The anti-caking or flow agent may include a bamboo extract that may include silica and carbohydrate. The bamboo extract may have a loose density (g/ml) of from about 0.14 g/ml to about 0.18 g/ml or a tapped density (g/ml) of from about 0.18 g/ml to about 0.22 g/ml. The bamboo extract may also include particles of the silica and the carbohydrate, wherein the particles have a size (Dv50) of from about 35 μm to about 55 μm. This anti-caking or flow agent may facilitate the manufacture, packaging, or storage of dry powdered food ingredients and food products such as spices, flavorings, and powdered food mixes as well as pharmaceuticals and nutraceuticals.

23 Claims, No Drawings

BAMBOO EXTRACT ANTI-CAKING AND FLOW AGENTS FOR DRY POWDERED FOODS, FOOD INGREDIENTS, PHARMACEUTICALS AND NUTRACEUTICALS

RELATED APPLICATIONS

The present application claims the benefit of priority to U.S. Patent Application No. 62/801,352, filed on Feb. 5, 2019; U.S. Patent Application No. 62/836,487, filed on Apr. 19, 2019; and U.S. Patent Application No. 62/949,602, filed on Dec. 18, 2019, the entire contents of each of which are incorporated herein by reference.

FIELD OF THE DISCLOSURE

This disclosure pertains to anti-caking and flow agents for dry powdered food ingredients and food products as well as pharmaceuticals and nutraceuticals.

BACKGROUND

Many food ingredients and food products such as spices, flavorings, and powdered food mixes as well as pharmaceuticals and nutraceuticals are prepared and marketed in generally dry powdered form. Such powdered ingredients and food products as well as pharmaceutical and nutraceutical products (referred to below as "dry powdered products"), may form lumps during their manufacture or packaging, or after storage. The formation of lumps in such dry powdered products may interfere with processing, manufacturing or use of such dry powdered products. Oftentimes, additional de-lumping process steps are required in the manufacture or handling of the dry powdered products.

Dry powdered products that contain substantial amounts of water-soluble amorphous substances are especially sensitive to caking since such substances are often hygroscopic. This problem is exacerbated in environments like kitchens and manufacturing environments with high relative humidity, particularly relative humidity levels over 50%. Furthermore, where there is a temperature gradient in the environment in which the dry powdered products are stored, increased water absorption may be experienced as moisture migrates from warmer surrounding regions into the dry powdered products.

For example, when consumers or manufacturers attempt to empty powdered spice, spice blends, pharmaceuticals or nutraceuticals from jars or bags, lumps which are present in the powder contained in the jars or bags may lead to difficulties in emptying them and hence to user dissatisfaction.

In order to facilitate the manufacture, packaging and handling of such dry powdered products, anti-caking and flow agents are often added to minimize caking and improve flowability. Anti-caking and flow agents are believed to reduce caking and improve flowability by competing with the powdered products for moisture, creating protective barriers on the surface of any hygroscopic particles present in the powdered products and coating powdered product surfaces to reduce inter-particle interactions.

Currently, the most widely used anti-caking/flow agent is silicon dioxide, which is generally considered a synthetic chemical additive. In light of consumers' ever-increasing demands for natural ingredients in food, pharmaceutical, or nutraceutical products, there is a need for a natural replacement for silicon dioxide. One natural replacement that has been suggested is ground rice hulls. Ground rice hulls, however, have been found to be substantially less effective in reducing caking and improving flowability than silicon dioxide. Additionally, ground rice hulls typically have a light brown or tan color, which makes this material undesirable in many applications. Discovery of different natural anti-caking and flow agents that are superior to ground rice hulls in these applications and can be properly labeled health nutrition friendly in accordance with government requirements would be an important and unexpected contribution to the manufacture and use of many dry powdered products. If such new natural anti-caking and flow agents were not only superior to ground rice hulls but also as good as or superior to silicon dioxide, a particularly important and unexpected contribution would be at hand. And, if such new natural anti-caking and flow agents were at least as effective as silicon dioxide at larger average particle sizes, dusting problems would be minimized thereby providing yet another important advantage. Embodiments of the present invention provide such unexpected contributions to the art.

BRIEF SUMMARY

An anti-caking or flow agent is provided that may include a bamboo extract comprising silica and carbohydrate. The bamboo extract may have a loose density (g/ml) of from about 0.14 g/ml to about 0.18 g/ml and/or a tapped density (g/ml) of from about 0.18 g/ml to about 0.22 g/ml. The bamboo extract may comprise particles having a size (Dv50) of from about 35 µm to about 55 µm.

A method of preparing the anti-caking or flow agent is provided. The method may include adding ground bamboo to water; heating the water to a temperature of about 70° C. to 80° C. for at least about three hours; removing the water from the ground bamboo to form a bamboo wet cake; drying the bamboo wet cake to form dried bamboo cake; and micronizing the dried bamboo cake.

A method of reducing caking in a dry powdered product is provided. The method may include adding the anti-caking or flow agent to the dry powdered product.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

DETAILED DESCRIPTION

Various embodiments are described below. The relationship and functioning of the various elements of the embodiments may better be understood by reference to the following detailed description. However, embodiments are not limited to those illustrated below. In certain instances, details may have been omitted that are not necessary for an understanding of embodiments disclosed herein.

An anti-caking or flow agent and methods of preparing the same are provided herein. The agent may be useful in preventing lump formation and caking in dry powdered products to enhance the processing, manufacturing, use, or storage of such dry powdered products.

The anti-caking or flow agent may include a bamboo extract comprising silica and carbohydrate. The silica and carbohydrate may be in the form of particles. The particle bulk properties of the bamboo extract may be selected based on the powder densities, namely the value where the entire population of bamboo extract particles resides within the identified densities. For particle bulk properties, this bulk property is referred to as loose (bulk) density or tapped (bulk) density, which is the mass (g)/volume (ml) when a powder is loosely filled into a graduated container and then tapped for a specified amount of time recording mass (g)/volume (ml) prior to and after tapping. Processes followed for identifying reported densities followed the ASTA method 25.0.

In some embodiments, the loose density (g/ml) of the natural anti-caking and flow agents may be from about 0.14 g/ml to about 0.18 g/ml, or from about 0.15 g/ml to about 0.17 g/ml, or to about 0.16 g/ml. In some embodiments, the loose density of natural anti-caking and flow agents may be about 0.15 g/ml. In some embodiments, the loose density of natural anti-caking and flow agents may be about 0.16 g/ml. The tapped density (g/ml) of the natural anti-caking and flow agents may be from about 0.18 g/ml to about 0.22 g/ml or from about 0.19 g/ml to about 0.21 g/ml. In some embodiments, the tapped density of the natural anti-caking and flow agents may be about 0.19 g/ml. In some embodiments, the tapped density of the natural anti-caking and flow agents may be about 0.20 g/ml. One set of preferred particle bulk properties at target Loose and Tapped Density (g/ml) values is set forth in Table I.

For purposes of embodiments of the present application, the particle size of the bamboo extract may be selected based on the median particle size, namely the value where half of the population of bamboo extract particles resides above the identified median, and half of the population of bamboo extract particles resides below the identified median. For particle volume, this volume median is referred to as Dv50, which is the size in microns lying in the volume with half above and half below the specified median diameter.

In some embodiments, Dv50 of the natural anti-caking and flow agents may be from about 35 μm to about 55 μm. In some embodiments, Dv50 of the natural anti-caking and flow agents may be from about 40 μm to about 50 μm. Preferably, Dv50 of the natural anti-caking and flow agents may be about 45 μm. Median particle sizes at target Dv50 values are set forth in Table II.

For purposes of embodiments of the present invention, the particle size of the bamboo extract may be selected based on the particle size distribution, namely the value that falls within two standard deviations of Dv50. For particle size distribution, this volume distribution is referred to as the Peak Width (μm), which is the size in microns at the 84$^{th}$ percentile less the size in microns at the 14$^{th}$ percentile.

In some embodiments, Peak Width (μm) of the natural anti-caking and flow agents may be from about 35 μm to about 75 μm or from about 45 μm to about 65 μm. In some embodiments, the Peak Width is about 55 μm. Particle size distribution values are set forth in Table II.

In some embodiments, the bamboo extract may have a Brunauer-Emmett-Teller (BET) surface area as measured by gas adsorption ranging from about 220 m$^2$/g to about 300 m$^2$/g. In some embodiments, the BET surface area may be about 250 m$^2$/g to about 270 m$^2$/g. In some embodiments, the BET surface area (m$^2$/g) of the natural anti-caking and flow agents may be from about 100 m$^2$/g to about 260 m$^2$/g.

In some embodiments, the t-Plot external surface area of the natural anti-caking and flow agents may be from about 100 m$^2$/g to about 200 m$^2$/g.

In some embodiments, the bamboo extract may have a pore area measured by mercury porosimetry ranging from 500 m$^2$/g to about 600 m$^2$/g. In some embodiments, the pore volume (mL/g) of the anti-caking and flow agents may be from about 0.05 mL/g to about 5.00 mL/g. In some embodiments, the pore diameter (μm) of the anti-caking and flow agents may be from about 0.001 μm to about 0.05 μm.

The natural anti-caking and flow agents of embodiments are prepared by subjecting bamboo to extraction processes that remove hot water soluble bamboo materials down to a level of about 60% by weight silica, with the balance believed to be primarily carbohydrate materials (naturally-occurring starches, sugars, and fibers) and trace minerals. In some embodiments, the bamboo extract comprises about 60 to about 90% by weight silica. Preferably, the water-soluble bamboo materials will be extracted down to a level of about 70-75% by weight silica and most preferably 75% by weight silica, with the balance believed to be primarily carbohydrate materials (naturally-occurring starches, sugars, and fibers) and trace minerals.

The bamboo subjected to extraction preferably will be *Phyllostachys virdis* or *Bambusa vulgaris* or a combination thereof but need not be limited to these preferred species.

Up to about 5% by weight of one or more additional carbohydrate moisture scavenging materials such as maltodextrin, or native corn, pea or rice starches, or other appropriate carbohydrates may be combined with the bamboo extracts. More than about 5% by weight is undesirable since it may interfere with the flow-enhancing properties of the bamboo extracts.

A method of preparing the anti-caking or flow agent of the present application is provided. The method may include adding ground bamboo to water; heating the water to a temperature of about 70° C. to 80° C. for at least about three hours; removing the water from the ground bamboo to form a bamboo wet cake; drying the bamboo wet cake to form dried bamboo cake; and micronizing the dried bamboo cake.

For example, the natural anti-caking and flow agents of embodiments may be prepared by grinding raw bamboo and placing the ground raw bamboo material in an extractor containing water (preferably distilled water) maintained at about 70 to 80° C. for at least about three hours, optionally with agitation as appropriate. The resulting mixture is then preferably centrifuged and filtered to leave a bamboo wet cake which will be dried, micronized, and heat sterilized preferably in a vacuum dryer. The resulting dry micronized material is then sieved and blended to meet particle size and particle size distribution requirements. The product is generally white, which is far preferred as a flow aid to the light brown or tan color of ground rice hulls in food applications where end product color is often a key consideration and light brown or tan ingredients are avoided if possible.

In alternative embodiments, the hot water extraction optionally may be modified by acidifying the water used in the extraction to an appropriate pH level.

The anti-caking or flow agents disclosed herein may be added to dry powder products such as, but not limited to, seasonings, pharmaceutical or nutraceutical products, or powdered foods. The anti-caking or flow agents may reduce or prevent caking and/or improve flowability of the dry powdered products to which they are added.

EXAMPLES

The following examples further illustrate and highlight embodiments of the invention but should not be construed as in any way limiting any aspect thereof.

Example 1. A FT4 Powder Rheometer was used to characterize flow and bulk properties of silicon dioxide, ground rice hulls and bamboo extracts in accordance with embodiments of the invention as anti-caking/flow aids. Basic Flow Energy (BFE, mJ) and Conditioned Bulk Density (CBD, g/ml) were identified as important in this evaluation through statistical analysis since they are of primary interest when studying how particle size/shape affects flow and bulk properties in a powder system.

Through size modification of bamboo extract prepared in accordance with embodiments of the invention, a direct relationship between particle size and BFE was identified comparing bamboo extracts in accordance with embodiments of the invention to not only silicon dioxide but also to calcium stearate and calcium silicate. If the effectiveness of bamboo extract particles of varying average particle sizes were tested for effectiveness vis-à-vis silicon dioxide particles of varying average particle sizes in improving flowability, it would be found that higher average micron particle sizes of the bamboo extract material lead to functionally similar BFEs of lower average micron particle sizes of silicon dioxide material. This data would also demonstrate that while the functionality of silicon dioxide as a flow aid requires the use of smaller average particle sizes, the functionality of bamboo extracts as a flow aid in accordance with the present disclosure requires the use of larger average particle sizes. Since larger particle size bamboo extracts can be used to replace smaller particle size silicon dioxide particles, the level of potentially problematic low particle size dust produced by flow aids can be reduced by replacing silicon dioxide flow aids with larger particle size bamboo extracts in accordance with embodiments of the invention. Results of BFE, FRI (Flow Rate Index) and density are shown in Table I.

The particle size and particle distribution was measured using a MICROTRAC instrument. Particle size and distribution are determined by passing a laser beam through a well-dispersed particle sample and detecting the intensity of the scattered light produced. The scattered light is measured at various angles up to 163 degrees.

Example 2. Water activity was used as an analytical measure to compare the moisture scavenging potential of silicon dioxide and bamboo extract anti-caking/flow aids of present disclosure. The water activity was first measured on fresh, unopened samples to generate a baseline. Then the materials were subjected to a high humidity atmosphere (60% RH for 24 hrs) forcing the product to uptake additional moisture. Following this, the materials were re-evaluated for water activity and moisture take up/physical changes that occurred were noted.

The data reported in Table III shows that silicon dioxide tested has a very weak moisture scavenging potential. This is reflected by the high starting water activity of the silicon dioxide which left little potential for additional moisture binding. Calcium stearate and calcium silicate have greater chemical affinity for moisture as shown and are more traditionally used as anti-caking aids (but not as flow aids since they are not as effective in this application). Carbohydrates such as native potato starch, maltodextrin tapioca, and potato maltodextrin show the greatest chemical affinity for moisture as shown and have also traditionally been used as anti-caking aids (but not as flow aids since they are not effective in this application). Unexpectedly, the bamboo extract showed greater affinity for moisture over all synthetic materials traditionally used for this purpose, including calcium stearate, and was found to be more comparative to the carbohydrates shown.

Example 3. VSA (vapor sorption analyzer) testing (which measures moisture isotherms) will confirm that the bamboo extract embodiments bind more water (g moisture/g product) than do synthetic materials including silicon dioxide, calcium stearate, and calcium silicate.

The porosity of Bamboo Extract, Rice Hulls, Calcium Silicate and various Silicon Dioxides were examined using three methods/equipment; Gas adsorption, Mercury porosimetry, and our current capability, Vapor Sorption Analyzer (VSA). SEM (Scanning Electron Microscopy) was also performed on the same materials also. Unexpectedly, the bamboo extract was found to have pore volume, surface area, and pore area values similar to commercially used silicon dioxides.

Surface area and pore size influence the porosity of powders. Gas adsorption is considered the gold standard for measuring surface area. Table IV is a summary of all the various measurements performed. BET surface area is a sum of the external surface area and internal micropore surface area. Rice Hulls have a much lower surface area ($m^2/g$) than the other materials at 1.8 $m^2/g$. Silicon Dioxide A is specified to have a surface area between 155 $m^2/g$ and 195 $m^2/g$. Bamboo extract has a surface area of 259 $m^2/g$. That number is in the same range as the other synthetic materials as they range from 132 $m^2/g$ to 462 $m^2/g$. Silicon Dioxide C is specified to have a surface area between 400-600 $m^2/g$. Silicon Dioxide C has a different function that Silicon Dioxide A and the larger surface area could be could be attributed to the increased water absorption for Silicon Dioxide C.

Again, the porosity of a material is a function of both internal and Extract structure. Mercury porosimetry is the gold standard for measuring internal properties related to porosity. Mercury porosimetry has a greater range than gas absorption. Pore volume (mL/g) and pore area ($m^2/g$) was measured. Rice Hulls does not have a large pore area at 4.1 $m^2/g$. It has the lowest pore area of all the materials analyzed. The next lowest pore area is 173 $m^2/g$ for Silicon Dioxide A. Bamboo extract has the highest pore area at 550 $m^2/g$. It is more comparable to Silicon Dioxide C, 499 $m^2/g$. The pore volume of these materials follows the same trend as Rice Hulls. Rice Hulls has a very low pore volume, 1.5 mL/g, while the other materials range from 3.9-5.8 mL/g. Bamboo extract, similarly to synthetic anti-caking agents, is a highly porous material. High pore volume and area correlate with increased water absorption and overall functionality.

Example 4. Table V reflects results obtained in an examination of the relative flow and water scavenging functionality of bamboo extract and ground rice hull particles in Roasted Onion and Classic Caesar Dry seasoning mixes. First, however, it should be noted that other tests demonstrated that when delivered at a level of three times that of the synthetic (silicon dioxide), the ground rice hull particles could not produce the required level of flowability in these dry seasoning mixes evident by the higher angle shown. Table V shows that the bamboo extract particles outperformed both the silicon dioxide and the rice hull particles in flowability and scavenging moisture. Bamboo extract was able to be used at up to a 40% reduction to that of silicon dioxide without significant sacrifice to flow or caking stability.

The use of the terms "a" and "an" and "the" and similar references in the context of describing embodiments are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable other unless otherwise indicated herein or otherwise clearly contradicted by context. The use of any and all examples, or exemplary language (i.e., "such as") provided herein, is intended merely to illuminate embodiments and does not pose a limitation on the scope of the embodiments.

Preferred embodiments are described herein. Variations of preferred embodiments may become apparent to those of ordinary skill in the art upon reading the foregoing description. The inventors expect skilled artisans to employ such variations as appropriate. Embodiments include all modifications, variations and equivalents of the subject matter described herein unless otherwise indicated herein or clearly contradicted by context as permitted by applicable law.

TABLE I

Flow and Bulk Properties $FT_4$ Flow and Bulk Properties

| Material Name | Statistics | BFE, mJ (S + VFR) | FRI | Loose Density, g/ml | Tapped Density, g/ml | Comments |
|---|---|---|---|---|---|---|
| SILICON DIOXIDE, PWDR A; Dv50 = 35.39 μm | AVG | 106.25 | 2.36 | 0.16 | 0.21 | Synthetic anti-caking and flow agent ingredient. Primarily used to modulate flow to a great degree in seasonings. |
|  | SD | 8.15 | 0.21 | 0.01 |  |  |
| SILICON DIOXIDE, PWDR B; Dv50 = 28.31 μm | AVG | 139.50 | 1.96 | 0.12 | 0.19 | Synthetic anti-caking and flow agent. |
|  | SD | 30.52 | 0.09 | 0.01 |  |  |
| CALCIUM STEARATE, PWDR | AVG | 124.14 | 2.30 | 0.36 | 0.26 | Synthetic moisture binding agent. |
|  | SD | 14.39 | 0.24 | 0.04 |  |  |
| CALCIUM SILICATE, PWDR | AVG | 82.33 | 2.03 | 0.12 | 0.13 | Synthetic moisture binding agent. |
|  | SD | 4.18 | 0.07 | 0.00 |  |  |
| BAMBOO EXTRACT; Dv50 = 46.22 μm | AVG | 120.75 | 2.00 | 0.16 | 0.21 | Demonstrates good flow/anti-caking properties. |
|  | SD | 2.22 | 0.07 | 0.00 |  |  |
| RICE HULL, PWDR | AVG | 391.21 | 2.37 | 0.37 | 0.56 | Clean label moisture binding agent. |
|  | SD | 13.12 | 0.23 | 0.01 |  |  |

TABLE II

Exemplary Bamboo Extract Article Specifications

Specification for Bamboo extract; Dv50 = 45 ± 10 μm

| | Particle Size - Volume per Light Scattering (%) | | | Distribution Band Width | | | | Bulk Properties - Loose and Tapped Density | | | |
|---|---|---|---|---|---|---|---|---|---|---|---|
| Percentile | Target (μm) | Min | Max | 100% | Target (μ) | Min | Max | | Target (g/ml) | Min | Max |
| Dv50 | 45 | 35 | 55 | Width | 55 | 35 | 75 | Loose | 0.16 | 0.14 | 0.18 |
|  |  |  |  |  |  |  |  | Tapped | 0.20 | 0.18 | 0.22 |

Preferred Specification for Bamboo extract; Dv50 = 45 ± 5 μm

| | Particle Size - Volume per Light Scattering (%) | | | Distribution - Band Width | | | | Bulk Property - Loose and Tapped Density | | | |
|---|---|---|---|---|---|---|---|---|---|---|---|
| Percentile | Target (μm) | Min | Max | 100% | Target (μ) | Min | Max | | Target (g/ml) | Min | Max |
| Dv50 | 45 | 40 | 50 | Width | 55 | 45 | 65 | Loose | 0.16 | 0.15 | 0.17 |
|  |  |  |  |  |  |  |  | Tapped | 0.20 | 0.19 | 0.21 |

TABLE III

Moisture Scavenging

| Material Name | Water Activity Upon Receipt | Water Activity 24 hrs in 60% RH | Free Moisture (%) Upon Receipt | Visual Description 24 hrs in 60% RH | Comments |
|---|---|---|---|---|---|
| SILICON DIOXIDE, PWDR A; Dv50 = 35.39 μm | 0.596 | 0.645 | 3.47 | Free flowing powder | Very weak to no moisture scavenging potential. |
| SILICON DIOXIDE, PWDR B; Dv50 = 28.31 μm | 0.532 | 0.650 | 5.74 | Free flowing powder | Weak moisture scavenging potential. |
| CALCIUM STEARATE, PWDR | 0.444 | 0.622 | <0.01 | Free flowing powder | Moderate moisture scavenging potential. |
| CALCIUM SILICATE, PWDR | 0.374 | 0.653 | 4.07 | Free flowing powder | Moderate moisture scavenging potential. |
| BAMBOO EXTRACT; Dv50 = 46.22 μm | 0.276 | 0.588 | 2.10 | Free flowing powder | Strong moisture scavenging potential. |
| MALTODEXTRIN, TAPIOCA | 0.246 | 0.610 | 2.72 | Free flowing powder | Strong moisture scavenging potential. |
| MALTODEXTRIN, POTATO | 0.170 | 0.614 | 3.36 | Free flowing powder | Strong moisture scavenging potential. |

TABLE IV

Porosity of Anti-Caking Agents and Flow-Aids

| | | SILICON DIOXIDE, PWDR A | | | SILICON DIOXIDE, PWDR B | | | SILICON DIOXIDE, PWDR C | | |
|---|---|---|---|---|---|---|---|---|---|---|
| | Parameters | VSA | Gas Adsorption | Mercury Porosimetry | VSA | Gas Adsorption | Mercury Porosimetry | VSA | Gas Adsorption | Mercury Porosimetry |
| Surface Area | BET Multiple, m²/g | 89.76 | 167.21 | — | 110.50 | 132.21 | — | 258.20 | 462.87 | — |
| | t-Plot external surface area, m²/g | 89.76 | 122.55 | — | 110.50 | 84.99 | — | 258.20 | 428.55 | — |
| Pore Size | Pore Volume, mL/g | 0.004 | 1.52 | 3.89 | 0.010 | 0.929 | 4.9920 | 0.330 | 1.95 | 5.09 |
| | Pore Diameter, μm | 0.075 | 0.04 | — | 0.092 | 0.05 | — | 0.010 | 0.02 | — |
| | Pore Area, m²/g | — | — | 173.83 | — | — | 296.36 | — | — | 498.77 |

| | | BAMBOO EXTRACT | | | RICE HULL, PWDR | | | CALCIUM SILICATE, PWDR | | |
|---|---|---|---|---|---|---|---|---|---|---|
| | Parameters | VSA | Gas Adsorption | Mercury Porosimetry | VSA | Gas Adsorption | Mercury Porosimetry | VSA | Gas Adsorption | Mercury Porosimetry |
| Surface Area | BET Multiple, m²/g | 101.7 | 259.0 | — | 117.80 | 1.8315 | — | 171.60 | 251.51 | — |
| | t-Plot external surface area, m²/g | 101.7 | 191.4 | — | 117.80 | 1.4893 | — | 171.60 | 158.5779 | — |
| Pore Size | Pore Volume, mL/g | 0.09 | 2.38 | 4.91 | 0.105 | 0.01 | 1.54 | 0.200 | 1.79 | 5.85 |

TABLE IV-continued

Porosity of Anti-Caking Agents and Flow-Aids

| | | | | | | | | | |
|---|---|---|---|---|---|---|---|---|---|
| Pore Diameter, μm | 0.004 | 0.04 | — | 0.005 | 0.022 | — | 0.010 | 0.03 | — |
| Pore Area, m²/g | — | — | 550.99 | — | — | 4.10 | — | — | 420.86 |

TABLE V

Seasoning Mix Results

| Formula Name | Functional Materials | Angle of Repose (avg n = 3) | Water Activity (n = 1) After Blending | Water Activity (n = 1) 24 hrs in 60% RH |
|---|---|---|---|---|
| Roasted Onion | Synthetic | 46.22 | 0.266 | 0.531 |
| | Bamboo <20% | 48.55 | 0.266 | 0.528 |
| | Bamboo <40% | 46.51 | 0.265 | 0.536 |
| | Rice Hulls (3:1) | 53.34 | 0.269 | 0.536 |
| Classic Caesar | Synthetic | 46.12 | 0.202 | 0.458 |
| | Bamboo <20% | 44.62 | 0.199 | 0.486 |
| | Bamboo <40% | 46.39 | 0.200 | 0.462 |
| | Rice Hulls (3:1) | 53.47 | 0.210 | 0.489 |

What is claimed is:

1. A composition for an anti-caking or flow agent, the composition comprising:
a micronized, fractionated bamboo extract comprising silica and carbohydrate, wherein the micronized, fractionated bamboo extract comprises a loose density (g/ml) of from about 0.14 g/ml to about 0.18 g/ml or a tapped density (g/ml) of from about 0.18 g/ml to about 0.22 g/ml.

2. The composition anti-caking or flow agent of claim 1, wherein the loose density is about 0.15 g/ml.

3. The composition anti-caking or flow agent of claim 1, wherein the tapped density is about 0.19 g/ml.

4. The composition anti-caking or flow agent of claim 1, wherein the micronized, fractionated bamboo extract comprises particles of the silica and the carbohydrate, wherein the particles have a size (Dv50) of from about 35 μm to about 55 μm.

5. The composition anti-caking or flow agent of claim 4, wherein the particles have a size of about 45 μm.

6. The composition anti-caking or flow agent of claim 1, wherein a peak width volume distribution of the anti-caking and flow agent is from about 35 μm to about 75 μm.

7. The composition anti-caking or flow agent of claim 1, wherein a peak width volume distribution of the anti-caking or flow agent is about 55 μm.

8. The composition anti-caking or flow agent of claim 1, wherein the micronized, fractionated bamboo extract comprises from about 60 to about 90% by weight silica.

9. The composition anti-caking or flow agent of claim 1, wherein the micronized, fractionated bamboo extract comprises about 75% by weight silica.

10. The composition anti-caking or flow agent of claim 1, wherein the micronized, fractionated bamboo extract comprises less than about 5% by weight of the carbohydrate.

11. The composition anti-caking or flow agent of claim 1, wherein the further comprising a second carbohydrate selected from the group consisting of is maltodextrin, native corn, pea or rice starches, or any combination thereof.

12. The composition anti-caking or flow agent of claim 1, wherein micronized, fractionated bamboo extract is derived from *Phyllostachys virdis, Bambusa vulgaris*, or a combination thereof.

13. The composition anti-caking or flow agent of claim 1 further comprising at least one seasoning.

14. The composition anti-caking or flow agent of claim 1 further comprising a pharmaceutical or nutraceutical.

15. A method of preparing the composition anti-caking or flow agent of claim 1, comprising:
adding ground bamboo to water;
heating the water to a temperature of about 70° C. to 80° C. for at least about three hours;
removing the water and water soluble bamboo fractions from the ground bamboo to form a fractionated bamboo wet cake;
drying the bamboo wet cake to form dried fractionated bamboo extract cake; and
micronizing the dried fractionated bamboo extract cake.

16. The method of claim 15, further comprising acidifying the water to an appropriate pH level before or after adding the ground bamboo to the water.

17. The method of claim 15 further comprising adding the composition anti-caking or flow agent of claim 1 to a dry powdered product.

18. A composition for an anti-caking or flow agent, the composition comprising:
a micronized, fractionated bamboo extract comprising silica and carbohydrate, wherein the bamboo extract comprises particles having a size (Dv50) of from about 35 μm to about 55 μm.

19. The composition anti-caking or flow agent of claim 18, wherein the particles comprise a peak width volume distribution from about 35 μm to about 75 μm.

20. The composition anti-caking or flow agent of claim 18, wherein the particles comprise a peak width volume distribution from about 35 μm to about 75 μm.

21. A method of preparing the composition anti-caking or flow agent of claim 18, comprising:
adding ground bamboo to water;
heating the water to a temperature of about 70° C. to 80° C. for at least about three hours;
removing the water from the ground bamboo to form a bamboo wet cake;
drying the bamboo wet cake to form dried bamboo extract cake;
micronizing the dried bamboo extract cake; and
sieving the micronized dried bamboo cake to obtain the micronized, fractionated bamboo extract.

22. The method of claim 21, further comprising acidifying the water to an appropriate pH level before or after adding the ground bamboo to the water.

23. The method of claim 15 further comprising adding the composition anti-caking or flow agent of claim 1 to a dry powdered product.

\* \* \* \* \*

UNITED STATES PATENT AND TRADEMARK OFFICE
CERTIFICATE OF CORRECTION

| | | |
|---|---|---|
| PATENT NO. | : 11,602,565 B2 | |
| APPLICATION NO. | : 16/782564 | |
| DATED | : March 14, 2023 | |
| INVENTOR(S) | : Gregory J. Meyers et al. | |

It is certified that error appears in the above-identified patent and that said Letters Patent is hereby corrected as shown below:

In the Specification

Column 8, Table I, Line 2, subtitle, delete "FT$_4$" and insert in its place --FT4--.

Column 8, Table 2, Line 2, middle column heading, delete "Distribution Band Width" and insert in its place --Distribution – Band Width--.

Signed and Sealed this
Thirtieth Day of May, 2023

Katherine Kelly Vidal
*Director of the United States Patent and Trademark Office*